US008583221B1

(12) United States Patent  
Patel et al.

(10) Patent No.: US 8,583,221 B1  
(45) Date of Patent: Nov. 12, 2013

(54) METHOD AND APPARATUS FOR DISPLAY OF CARDIAC SIGNAL EPISODES WITH OVER- OR UNDER-SENSING

(75) Inventors: Amisha S. Patel, Maple Grove, MN (US); Bruce D. Gunderson, Plymouth, MN (US); Mark L. Brown, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/456,828

(22) Filed: Apr. 26, 2012

(51) Int. Cl.
*A61B 5/04* (2006.01)

(52) U.S. Cl.
USPC .......................................................... 600/521

(58) Field of Classification Search
USPC .......................................................... 600/521
See application file for complete search history.

(56) References Cited

U.S. PATENT DOCUMENTS

| | | | |
|---|---|---|---|
| 4,374,382 A | 2/1983 | Markowitz | |
| 5,117,824 A | 6/1992 | Keimel | |
| 5,755,736 A | 5/1998 | Gillberg | |
| 6,052,620 A | 4/2000 | Gillberg | |
| 6,178,350 B1 | 1/2001 | Gillberg et al. | |
| 6,249,701 B1 | 6/2001 | Rajasekhar | |
| 6,418,346 B1 | 7/2002 | Nelson | |
| 6,442,433 B1 | 8/2002 | Linberg | |
| 6,480,745 B2 | 11/2002 | Nelson | |
| 6,599,250 B2 | 7/2003 | Webb | |
| 7,783,354 B2 | 8/2010 | Gunderson | |
| 7,831,304 B2 | 11/2010 | Cao | |
| 8,073,536 B2 | 12/2011 | Gunderson | |
| 8,073,537 B2 | 12/2011 | Gunderson | |
| 2007/0135864 A1* | 6/2007 | Gunderson et al. | 607/59 |
| 2008/0270036 A1* | 10/2008 | Webb et al. | 702/19 |
| 2009/0292218 A1* | 11/2009 | Diem et al. | 600/523 |
| 2009/0292331 A1 | 11/2009 | Gunderson | |
| 2011/0196247 A1 | 8/2011 | Cao | |

OTHER PUBLICATIONS

Purerfellner H., et al., "Accuracy of atrial tachyarrhythmia detection in implantable devices with arrhythmia therapies", Pacing Clin Electrophysiol. Jul. 2004;27(7):983-92.

Gunderson BD, et al., "Development of a post-processing alogrithm to classify rhythms detected as ventricular tachyarrhythmias by implantable cardioverter defibrillators", Computers in Cardiology, 2007, pp. 797-800, vol. 34.

* cited by examiner

*Primary Examiner* — Christopher D Koharski  
*Assistant Examiner* — Michael Carey  
(74) *Attorney, Agent, or Firm* — Michael C. Soldner (57) ABSTRACT

A medical device system senses cardiac signals and generates and stores sensing data including sensed cardiac events. A processor receiving the sensing data is configured to detect undersensed and oversensed events. The processor generates an episode display comprising event identifying codes in response to the received sensing data and produces an adjusted episode display in response to an event being identified as an undersensed event or an oversensed event.

17 Claims, 7 Drawing Sheets

METHOD AND APPARATUS FOR DISPLAY OF CARDIAC SIGNAL EPISODES WITH OVER- OR UNDER-SENSING

FIELD OF THE DISCLOSURE

The disclosure relates generally to medical devices and, in particular, to an apparatus and method for generating a clean display of sensed event signal data when undersensing or oversensing of a cardiac signal is detected.

BACKGROUND

Implantable medical devices (IMDs), including pacemakers and cardioverter-defibrillators (ICDs), record cardiac electrogram (EGM) signals for detecting the heart rhythm and responding as needed with pacing therapy or high-voltage cardioversion/defibrillation therapy. Episodes of the EGM signals are typically stored in the memory of the IMD, particularly when a tachyarrhythmia is detected by the IMD. Reviewing episode data stored in the IMD by a clinician provides the clinician with valuable information for diagnosing the patient's condition and selecting the best treatment options for the patient. To enable the clinician to efficiently identify electrical events on the EGM signal as they are sensed by the IMD, a Marker Channel® (Medtronic, Inc., Minneapolis Minn.) can be displayed to provide indentifying event markers and corresponding annotation of events occurring during stored episodes of EGM data. The Marker Channel data may be transmitted from the IMD to an external interrogating programmer through wireless telemetric communication. The event identification markers and corresponding annotation identify various events as interpreted by the IMD are displayed by the programmer. Events identified and displayed may include atrial sense events (AS), atrial pace events (AP), ventricular sense events (VS), and ventricular pacing events (VP), and refractory sense events (VSR or ASR).

In some cases undersensing or oversensing of cardiac events on the EGM signal occurs. On an atrial sensing channel, P-waves may be undersensed or far field R-waves (FFRWs) may be oversensed leading to erroneous cardiac interval measurements and heart rate detection. On the ventricular sensing channel, undersensing of R-waves or oversensing of T-waves can occur. Oversensing of non-cardiac noise can also occur. In a Marker Channel display, the sensed events are displayed and labeled as "seen" by the IMD. As such, a clinician or other user reviewing an episode will see the Marker Channel events as sensed by the IMD, which may omit undersensed events and include oversensed events labeled as AS or VS events. In this situation, the clinician is presented with inaccurate event rates and patterns, limiting the ability to efficiently and accurately identify the patterns and rhythms actually presented by the patient without careful manual analysis of the EGM signal itself.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
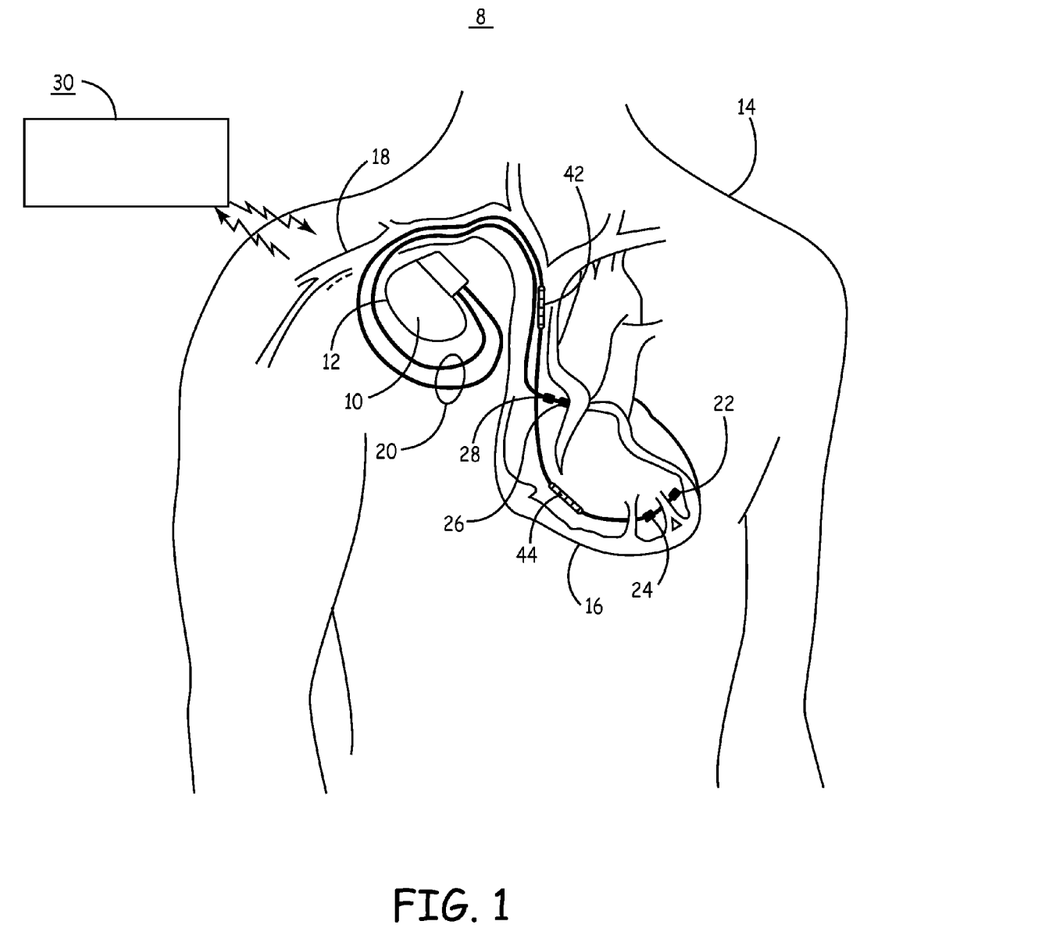
FIG. 1 is a schematic diagram of an implantable medical device system according to one embodiment.

FIG. 1 is a schematic diagram of an implantable medical device system 8 according to one embodiment. As illustrated in FIG. 1, a system 8 for sensing cardiac events and generating an encoded identification marker display of the events includes an implantable medical device (IMD) 10, such as an ICD capable of delivering pacing, cardioversion and defibrillation therapy to the heart 16 of a patient 14. One or more leads, collectively identified with reference numeral 20 in FIG. 1, are electrically coupled to the IMD 10 and extend into the patient's heart 16 via a vein 18. Leads 20 include electrodes 22 and 24 shown positioned in the patient's right ventricle (RV) and electrodes 26 and 28 positioned in the patient's right atrium (RA). When embodied as an ICD, leads 20 additionally carry high voltage coil electrodes 42 and 44 used to deliver cardioversion or defibrillation shock pulses. The leads 20 are used to acquire intracardiac EGM signals from the patient 14 and to deliver therapy in response to the acquired data.

IMD circuitry and associated battery(ies) are housed within a sealed housing 12, which may itself be conductive so as to serve as an electrode for use as an indifferent electrode during pacing or sensing or as an active electrode during defibrillation. As such, housing 12 is also referred to herein as "housing electrode" 12.

The IMD 10 may be implemented as other medical devices, such as a pacemaker, a drug delivery system, a cardiac monitor, a neurostimulator or any other device which includes sensing capabilities and electrodes for acquiring signals of cardiac electrical events. The embodiments described herein relate primarily to acquiring cardiac EGM signals, classifying cardiac events sensed on the EGM signals, and displaying an episode of sensed cardiac events including annotated event identification codes, which may include, but is not limited to, logic level marker signals, annotations of the markers, event interval measurements, and event numbers or time stamps. The techniques disclosed herein, however, may be applied to other electrical or mechanical signals from which physiological events are sensed, such as ECG signals, EMG signals, blood pressure signals, or heart sound signals.

The EGM signal data is acquired by IMD 10 and can be transmitted to an external device 30, which may be embodied as a programmer, e.g. used in a clinic or hospital to communicate with IMD 10 via wireless telemetry. External device 30 may alternatively be embodied as a computer, home monitor, or hand-held device including a cell phone, smart phone or other hand-held device, enabled to communicate directly or indirectly with IMD 10 for retrieving EGM signal data acquired by IMD 10.

Figure 2:
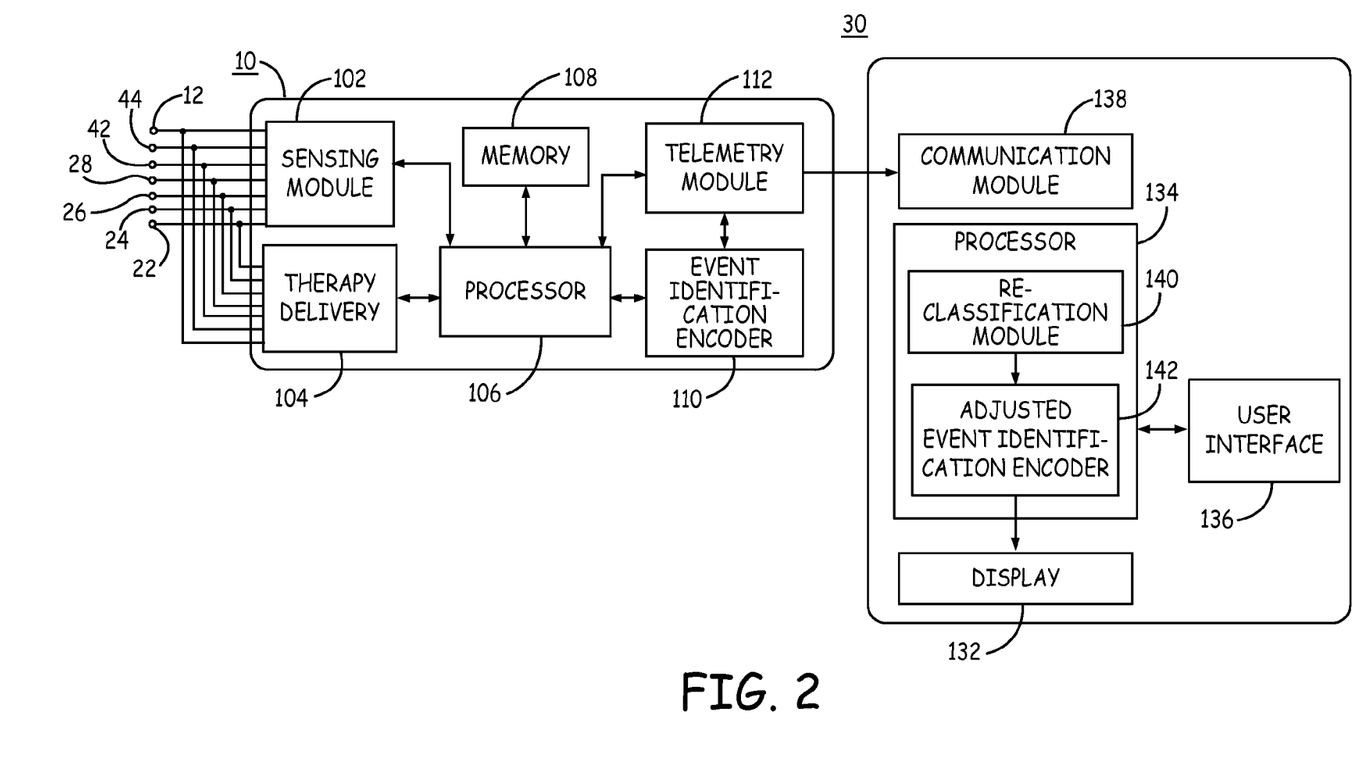
FIG. 2 is a functional block diagram of the system of FIG. 1 according to one embodiment.

FIG. 2 is a functional block diagram of system 8 according to one embodiment. IMD 10 includes a sensing module 102, a therapy delivery module 104, a processor 106 and associated memory 108, an event identification encoder 110, and a telemetry module 112.

Memory 108 may include computer-readable instructions that, when executed by processor 106, cause IMD 10 and processor 106 to perform various functions attributed throughout this disclosure to IMD 10, processor 106, and event identification encoder 110. The computer-readable instructions may be encoded within memory 108. Memory 108 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 106 and other processor units described herein may include any one or more of a microprocessor, a controller, a digital signal processor (DSP), an application specific integrated circuit (ASIC), a field-programmable gate array (FPGA), or equivalent discrete or integrated logic circuitry. In some examples, processor 106 may include multiple components, such as any combination of one or more microprocessors, one or more controllers, one or more DSPs, one or more ASICs, or one or more FPGAs, as well as other discrete or integrated logic circuitry. The functions attributed to processor 106 herein may be embodied as software, firmware, hardware or any combination thereof. In one example, event identification encoder 110 may, at least in part, be stored or encoded as instructions in memory 108 that are executed by processor 106.

Processor 106 includes a therapy control unit that controls therapy delivery module 104 to deliver electrical stimulation therapy, e.g., cardiac pacing or anti-tachyarrhythmia therapy to heart 16 according to a selected one or more therapy programs, which may be stored in memory 108. Therapy delivery module 104 is electrically coupled to electrodes 22, 24, 26, 28, 42, 44 and housing electrode 12 (all of which are shown in FIG. 1). Therapy delivery module 104 is configured to generate and deliver electrical stimulation therapy to heart 16 via selected combinations of electrodes 22, 24, 26, 28, 42, 44, and housing electrode 12.

Sensing module 102 monitors cardiac electrical signals for sensing cardiac electrical events, e.g. P-waves and R-waves, from selected ones of electrodes 22, 24, 26, 28, 42, 44, and housing electrode 12 in order to monitor electrical activity of heart 16. Sensing module 102 may include a switch module to select which of the available electrodes are used to sense the cardiac electrical activity. The switch module may include a switch array, switch matrix, multiplexer, or any other type of switching device suitable to selectively couple electrodes to sensing module 102. In some examples, processor 106 selects the electrodes to function as sense electrodes, or the sensing vector, via the switch module within sensing module 102.

Sensing module 102 includes multiple sensing channels, each of which may be selectively coupled to respective combinations of electrodes 22, 24, 26, 28, 42, 44 and housing 12 to detect electrical activity of a particular chamber of heart 16. Each sensing channel may comprise an amplifier that outputs an indication to processor 80 in response to sensing of a cardiac depolarization, in the respective chamber of heart 16. In this manner, processor 106 may receive sense event signals corresponding to the occurrence of R-waves and P-waves in the various chambers of heart 16. Sensing module 102 may further include digital signal processing circuitry for providing processor 106 with digitized EGM signals.

Memory 108 stores intervals, counters, or other data used by processor 106 to control the delivery of pacing pulses by therapy delivery module 104 Such data may include intervals and counters used by processor 106 to control the delivery of pacing pulses to heart 16. The intervals and/or counters are, in some examples, used by processor 106 to control the timing of delivery of pacing pulses relative to an intrinsic or paced event in another chamber. Memory 108 also stores intervals for controlling cardiac sensing functions such as blanking intervals and refractory sensing intervals. Events sensed by the sense amplifiers are identified based on their occurrence outside a blanking interval and inside or outside of a refractory sensing interval.

Event identification encoder 110 receives the sense signals corresponding to R-waves and P-waves from sensing module 102 or processor 106 and generates coded identification data of each sensed event. For example, sensing module 102 may output different logic level signals distinguishing between sensed events such as atrial sensed events, atrial refractory sensed events, ventricular sensed events and ventricular refractory sensed events. In response to the logic signals, event identification encoder 110 generates encoded data in a serial format to transmit to the telemetry module 112, for further transmission to programmer 30. The encoded data includes event markers in the form of logic level signals annotated with initials such as AS (atrial sense), ASR (atrial refractory sense), VS (ventricular sense) or VSR (ventricular refractory sense). Event identification encoder 110 may incorporate pacing events in the annotated logic level signals, including ventricular pacing pulse (VP) and atrial pacing pulse (AP) markers.

In various embodiments, event identification encoder 110 may be implemented as digital logic circuitry or executable code stored in memory 108 executed by processor 106. Event identification encoder 110 may correspond generally to the marker channel logic disclosed in U.S. Pat. No. 4,374,382 (Markowitz), hereby incorporated herein by reference in its entirety. In other embodiments, sense event signals produced by sensing module 102 may be transmitted to programmer 30 and external processor 134 may perform the operations required for generating encoded event identification data for displaying and identifying events sensed by IMD 10 during a recorded EGM episode.

Programmer 30 includes a display 132, a processor 134, a user interface 136 and a communication module 138. A user, such as a physician, technician, nurse or other clinician, may interact with programmer 30 via user interface 36. For example, the user may interact with programmer 30 to retrieve currently programmed operating parameters, physiological data including EGM signal data collected by IMD 10, or device-related diagnostic information from IMD 10. A user may also interact with programmer 30 to program IMD 10, e.g., select values for operating parameters controlling the function of IMD 10. A user interacting with programmer 30 may interrogate IMD 10 to retrieve and view a display of a recorded EGM signal with accompanying encoded event identification data to review and evaluate episodes of the EGM signal data. Typically, episodes of recorded EGM signal data will be episodes which have been detected as an arrhythmia by IMD 10, which may be a bradycardia, tachycardia or fibrillation episode in some examples. User interface 36 may include a mouse, pointer, keyboard, touch screen or any combination thereof for enabling a user to interact with programmer 30 to select programmer functions such as selecting EGM signal data to be displayed and the type of display or format to be viewed. As will be described further below, a user may select the format of encoded event identification markers to be displayed in a Marker Channel that has been corrected for undersensing or oversensing.

Programmer 30 includes a communication module 138 to enable wireless communication with IMD 10. Examples of communication techniques used by system 8 include low frequency or radiofrequency (RF) telemetry, which may be an RF link established via Bluetooth, WiFi, or MICS. Programmer 30 may include a programming head that is placed proximate to the patient's body near the IMD 10 implant site, and in other examples programmer 30 and IMD 10 may be configured to communicate using a distance telemetry algorithm and circuitry that do not require the use of a programming head and do not require user intervention to establish or maintain a communication link.

It is contemplated that programmer 30 may be coupled to a communications network via communications module 138 for transferring data to a remote database or computer to allow remote monitoring and management of patient 14 using the techniques described herein. Reference is made to commonly-assigned U.S. Pat. Nos. 6,599,250 (Webb et al.), 6,442,433 (Linberg et al.), 6,418,346 (Nelson et al.), and 6,480,745 (Nelson et al.) for general descriptions and examples of network communication systems for use with implantable medical devices for remote patient monitoring and device programming, all of which patents are hereby incorporated herein by reference in their entirety. Remote patient management systems, such as the Carelink® Network (Medtronic, Inc., Minneapolis, Minn., USA) may be configured to utilize the presently disclosed techniques to enable a clinician to review EGM signal data with encoded event identification data that has been corrected or adjusted to account for undersensing and/or oversensing detected during post-processing of the sensed event signals and EGM signal data.

The classification of sensed events from EGM signals is initially performed by IMD 10 according to one embodiment. Events are sensed by sensing module 102, which includes sense amplifiers with automatic adjusting sensing thresholds, for example as disclosed in U.S. Pat. No. 5,117,824 (Keimel et al.) and U.S. Pat. No. 6,249,701 (Rajasekhar, et al.). An atrial sense amplifier and a ventricular sense amplifier receive EGM signals from selected electrodes 22, 24, 26, 28, 42, 44 and 12 and provide P-wave sense and R-wave sense output signals to event identification encoder 110 for use in generating the encoded event markers. As will be described herein, detected episodes may be re-classified by reclassification module 140 included in programmer processor 134. Detected episodes may be reclassified based on an analysis of the sensed signals and/or digitized EGM signals for evidence of undersensing and oversensing or P-waves and/or R-waves.

An adjusted event identification encoder 142 receives the encoded sensed event data from event identification encoder 110 via telemetric communication and event reclassification data from module 140. Adjusted event identification encoder 142 then generates adjusted event identification markers and associated annotation to display a Marker Channel that is corrected for any undersensed events and oversensed events detected by reclassification module 140.

Processor 134 generates a display of the classified sensed events on display 32. A user interacting with user interface 136 may select the display type or format of event identifying markers. For example, the user may be presented with display options including the original Marker Channel display showing encoded event identification markers as originally identified by the IMD 10 or an adjusted Marker Channel display showing the event identification markers corrected for undersensing and/or oversensing after any reclassification of sensed events by module 140. Corrected event identification markers can include event markers added due to the detection of undersensing and event markers that are removed due to the detection of oversensing.

In addition to reclassifying and adjusting (adding, removing or reformatting) encoded event identification markers, event intervals may be recomputed by processor 134. Corrected event intervals may be displayed in the corrected Marker Channel display.

The operations described herein for classifying events, reclassifying events, and generating a display including adjusted event identification markers based on an analysis for detecting undersensing and oversensing may be performed entirely by processor 134 or in a distributed manner between IMD processor 106, event identification encoder 110, and programmer processor 134. In some embodiments, a processor generating the display of classified events and adjusting the display in response to reclassifying events as undersensed or oversensed events may be located remotely from patient 14 and programmer 30. In this case, sensed event signals and EGM signal data may be transmitted from IMD 10 to a remote processor via programmer 30 and a communication network, for example via the Internet or the Carelink® Network.

Figure 3:
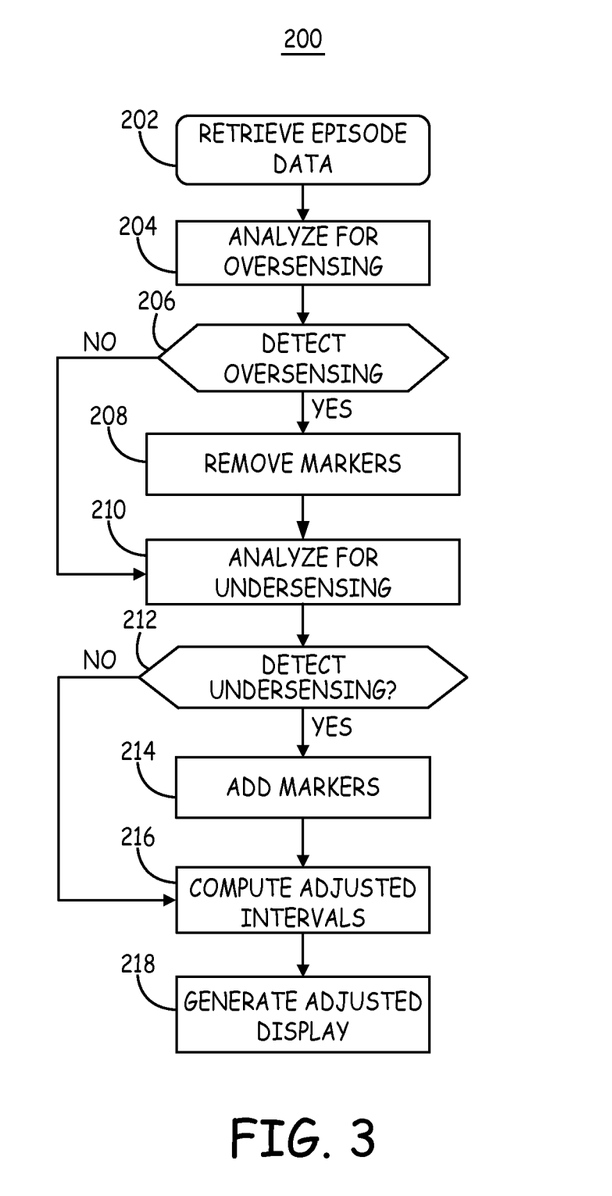
FIG. 3 is a flow chart of a method for generating a display of encoded event identification markers according to one embodiment.

FIG. 3 is a flow chart 200 of a method for generating a display of encoded sensed event markers according to one embodiment. Flow chart 200 and other flow charts presented herein are intended to illustrate the functional operation of the IMD system, and should not be construed as reflective of a specific form of software or hardware necessary to practice the methods described. It is believed that the particular form of software will be determined primarily by the particular system architecture employed in the device. Providing software to accomplish the described functionality in the context of any modern IMD system, given the disclosure herein, is within the abilities of one of skill in the art.

Methods described in conjunction with flow charts presented herein may be implemented in a non-transitory computer-readable medium that includes instructions for causing a programmable processor to carry out the methods described. A non-transitory computer-readable medium includes but is not limited to any volatile or non-volatile media, such as a RAM, ROM, CD-ROM, NVRAM, EEPROM, flash memory, or other computer-readable media, with the sole exception being a transitory, propagating signal. The instructions may be implemented as one or more software modules, which may be executed by themselves or in combination with other software.

At block 202, EGM episode data is retrieved from IMD 10 by programmer 30. The EGM episode data may include a recording of the EGM signal and encoded identification markers indicating sensed (and paced) events. The episode data is analyzed at block 204 to detect possible incidences of oversensing. One method for detecting oversensing will be described in conjunction with FIG. 4. Briefly, in one embodiment, analysis for detecting oversensing may include an analysis of event intervals and a correlation between atrial and ventricular events. If oversensing is detected on a sensing channel at block 206, event identification markers are removed from the Marker Channel data received from the IMD 10 to produce an adjusted Marker Channel at block 208.

The practice of reclassifying sensed events and adjusting encoded event identification markers in a Marker Channel display is not limited to one particular method for detecting oversensing or undersensing. Any method for detecting oversensing of cardiac or non-cardiac events may be employed. Oversensing of cardiac events may include sensing far-field R-waves (FFRWs) as P-waves on the atrial sensing channel or sensing T-waves as R-waves on the ventricular sensing channel. Oversensing of non-cardiac events may include sensing of electromagnetic interference, oversensing due to lead-related issues such as lead fracture, or oversensing of non-cardiac muscle noise.

At block 210, the EGM episode data is evaluated for undersensing. A method for detecting undersensing will be described in greater detail in conjunction with FIG. 5. Undersensing occurs when a true P-wave is not sensed by the atrial channel or a true R-wave is not sensed by the ventricular channel. Briefly, event intervals and patterns may be evaluated for identifying any event intervals that are relatively long compared to other event intervals within the same episode. Criteria for detecting undersensing may include any event interval longer than a threshold interval or a total number of events in the episode of a known time duration less than a threshold number of events expected to occur during that time duration.

If undersensing is detected, as determined at block 212, the adjusted event identification encoder 142 will perform a process of adding an event marker during each interval identified as an undersensed event interval at block 214. A method for adding event markers in an adjusted Marker Channel will be described in conjunction with FIG. 5.

After removing and/or adding event markers in response to detecting oversensed events or undersensed intervals, respectively, the adjusted event identification encoder 142 computes new event intervals using the adjusted event markers at block 216. In addition to computing the new event intervals, all event markers in the adjusted Marker Channel may be renumbered consecutively in the episode to account for any removed or added event markers.

At block 218, a display of the adjusted Marker Channel is generated. The adjusted Marker Channel display may be a corrected display of encoded event identification markers that displays added event markers associated with undersensed intervals and does not display removed event markers associated with oversensed events. In other words, an adjusted Marker Channel may be displayed to a user without any indication of what events have been added or removed or which intervals have been recomputed.

In other embodiments, the adjusted display generated at block 218 may include color-coding, shading, outlining or other formatting to distinguish added event markers, the locations of removed event markers, recomputed event intervals, and/or renumbered events from the original Marker Channel output received from the IMD 10. A user may be able to select how the adjusted Marker Channel is displayed and may be able to toggle between any combination of an original, uncorrected Marker Channel display, an adjusted Marker Channel display without formatting to indicate corrections or adjustments made to the original Marker Channel, and an adjusted Marker Channel display with formatting to distinctly identify adjustments made to the original Marker Channel to correct for detected undersensing and/or oversensing.

Figure 4:
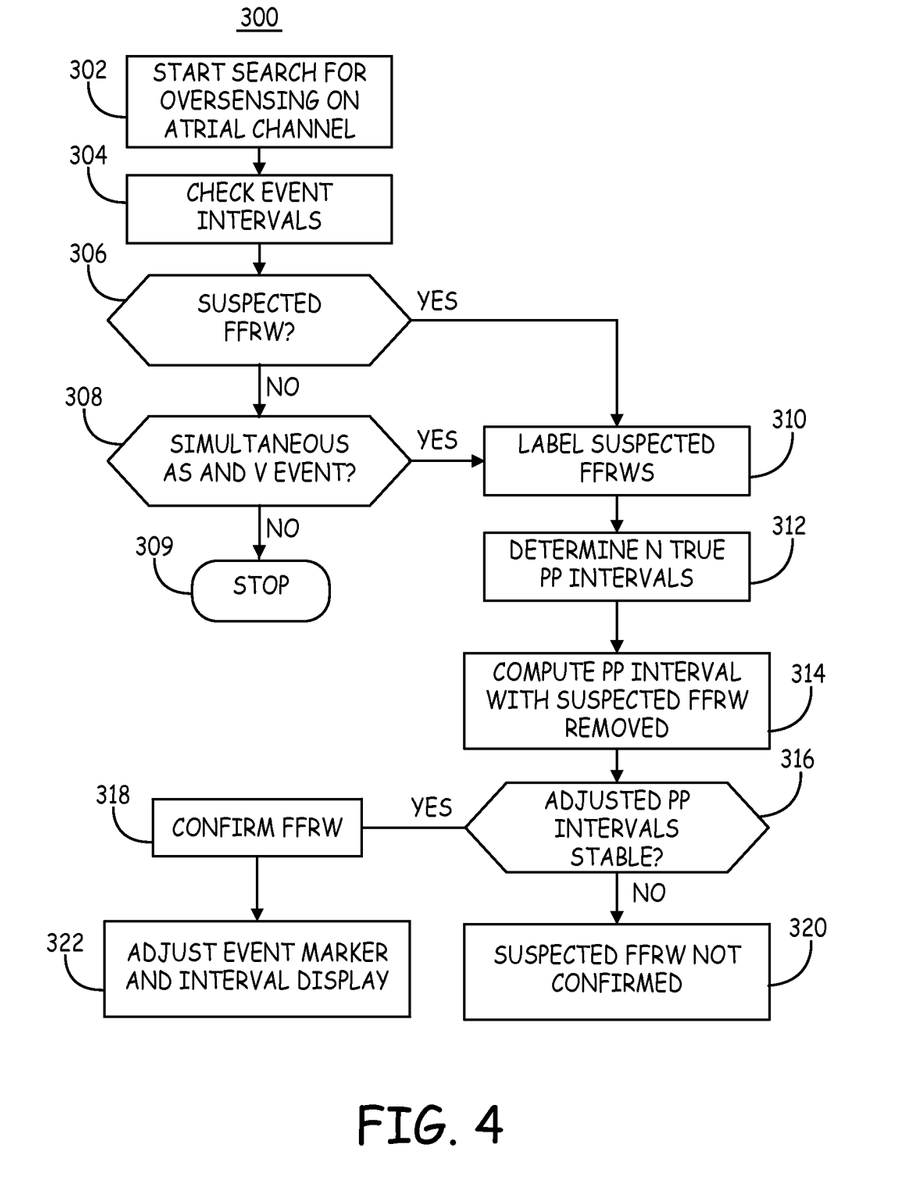
FIG. 4 is a flow chart for detecting oversensed events according to one embodiment.

FIG. 4 is a flow chart 300 of a method for detecting oversensed events according to one embodiment and generating an adjusted Marker Channel display of corrected sensed event identification markers. The example shown in flow chart 300 relates to detecting oversensing of far-field R-waves on an atrial sensing channel. At block 302, the processor 134 begins a search of the atrial channel sensed events for sensed events suspected to be FFRWs. An initial search for FFRWs may include comparing event intervals at block 304, which may include PP intervals, PR intervals and/or RP intervals. Examples of methods for detecting oversensing of FFRWs that may be implemented in the presently disclosed system are described in U.S. Pat. No. 6,178,350 to Gillberg et al., U.S. Pat. No. 6,052,620 to Gillberg et al., and U.S. Pat. No. 5,755,736 to Gillberg et al., all of which are hereby incorporated herein by reference in their entireties. Suspected FFRWs based on interval analysis are identified at block 306.

In addition or alternatively to analyzing event intervals, other factors may be utilized by the programmer 30 to identify suspected FFRWs at block 308, such as instances of approximately simultaneous atrial sense (AS) and ventricular events, except in instances where the ventricular event is an anti-tachycardia ventricular pacing pulse. Suspected FFRWs may be identified before and after a detection of a tachyarrhythmia by the IMD 10 during the EGM episode.

Suspected FFRWs are labeled at block 310. A predetermined number of PP intervals are measured between AS events that have not been labeled as suspected FFRWs at block 312 to obtain a "true" PP interval. At block 314, any suspected FFRWs are ignored for the purposes of computing resulting PP intervals in which oversensing is suspected. If a predetermined number of consecutive PP intervals with the suspected FFRWs removed are stable (decision block 316), for example consecutive PP intervals are equal to or less than 110% of the true PP intervals, the suspected FFRWs are confirmed as oversensed FFRWs at block 318. If the adjusted PP intervals with suspected FFRWs removed do not meet stability criterion, the suspected FFRW is not confirmed (block 320). Any AS event(s) labeled as suspected FFRWs will remain classified as AS event(s) and displayed as AS events according to a logic level marker convention in a Marker Channel display.

In response to confirming a suspected FFRW at block 318, an adjusted display of event identification markers and corresponding event intervals is generated at block 322. Event markers corresponding to a confirmed FFRW are either removed or modified to no longer indicate a true atrial sensed event. The event interval in which oversensing occurred is recomputed ignoring the oversensed event and the adjusted event interval measurement is included in the adjusted Marker Channel display.

In addition to examining event intervals, a morphology analysis may be performed to detect or confirm suspected FFRWs. For example, after identifying a suspected FFRW, the morphology of the atrial EGM signal corresponding in time to the suspected FFRW may be compared to a true P-wave morphology template or a known FFRW morphology template to confirm the FFRW. The methods for detecting oversensing and undersensing as generally disclosed in U.S. Pat. No. 8,073,536 (Gunderson, et al.) and U.S. Pat. No. 8,073,537 (Gunderson, et al.) may be implemented in the presently disclosed system for use in generating an adjusted Marker Channel display. The '536 and '537 patents are incorporated herein by reference in their entirety.

In addition to or alternatively to searching for oversensing in the atrial channel, the ventricular events from the Marker Channel may be analyzed for detecting oversensing in the ventricular channel. In a search for suspected oversensing of ventricular events, the EGM signal amplitude of VS events, the signal width, other aspects the EGM signal morphology corresponding to a VS event, or an overall morphology matching score when comparing an event to a known R-wave or other known template such as a T-wave template, may be used for identifying suspected oversensed events. Event interval analysis may be performed with suspected oversensed events ignored to determine whether event intervals are stable with the suspected oversensed events removed in order to confirm the oversensed events. In an adjusted display of ventricular event identification makers, oversensed events may be removed or formatted in a manner to distinguish from "true" sensed events. Event intervals may be re-computed, ignoring the oversensed events.

Figure 5:
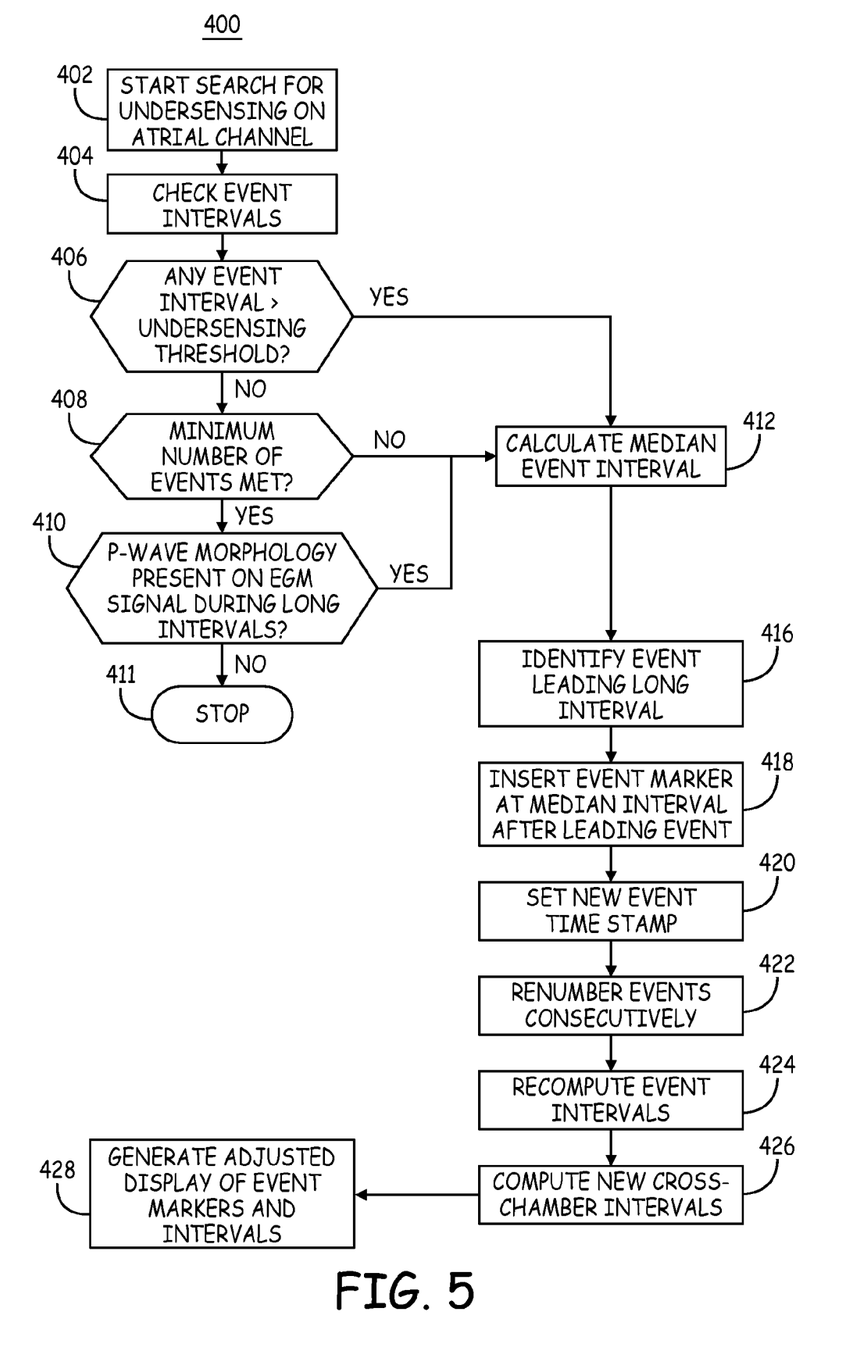
FIG. 5 is a flow chart of a method for detecting undersensing and correcting a display of encoded event identification markers of sensed events.

FIG. 5 is a flow chart 400 of a method for detecting undersensing and correcting encoded event identification markers of sensed events for display in a Marker Channel. At block 402, a search for undersensed events is initiated. In the illustrative example, post-processing of atrial channel sensing data received from the IMD is performed by programmer 30 for detecting undersensing of P-waves. The techniques described may be adapted, however, for use in detecting undersensing of R-waves in a ventricular sensing channel. At block 404, sensed event intervals are analyzed to detect intervals or patterns that are indicative of possible undersensing.

For example, if any event interval is greater than an undersensing threshold interval, as determined at decision block 406, undersensing is detected. An undersensing threshold may be defined as a fixed value corresponding to a relatively long PP interval, e.g. 2,500 ms. An undersensing threshold may additionally or alternatively be defined as a percentage greater than a previous PP interval or an average of previous PP intervals. If one or more event intervals meet an undersensing threshold criterion applied at block 406, which may include applying one or more undersensing thresholds, undersensing is detected and the process advances to block 412.

If event intervals do not meet undersensing threshold criteria applied at block 406, the number of sensed events during a recorded episode may be examined at decision block 408. The number of sensed events may be examined before and/or after detection of a tachyarrhythmia. If a minimum number of events are sensed for the given episode, then there is no indication of undersensing, and the process advances to block 410.

If, however, a minimum number of sensed events are not present in the recorded episode, before and/or after detection of a tachyarrhythmia, atrial undersensing is detected and the process advances to block 412. A minimum number of sensed events may be based on a total time interval of the recorded episode, a frequency of expected events, or a number of ventricular events sensed during the recorded episode. To illustrate, suppose a recorded episode is approximately 10 seconds long, a minimum of 9 sensed events may be expected on the atrial channel. If less than 9 sensed events are present, atrial undersensing is detected.

In some embodiments, a search for possible undersensing may include an EGM signal morphology analysis at block 410. If a P-wave morphology is present during an event interval found to be longer than an undersensing threshold interval, undersensing is detected. In this case, an undersensing threshold interval may be defined as a fixed amount or a percentage greater than a median atrial event interval computed from a number of previous event intervals. In one embodiment, the threshold is a percentage of the median interval where the percentage applied is inversely scaled to the median interval. For example if the median interval is very short, e.g. less than 200 ms, the current atrial interval must be more than three times greater the median atrial interval and a P-wave morphology must be present in the atrial EGM signal in order to detect undersensing. If the median interval is relatively long, e.g. greater than 350 ms, the current atrial interval must be more than 1.7 times greater than the median interval and a P-wave morphology must be present during the interval for undersensing to be detected. Other examples of useful methods for detecting atrial undersensing are disclosed in the above-incorporated '536 and '537 patents.

If undersensing is not detected based on the applied undersensing detection criteria, the process is terminated at block 411. No corrections or adjustments for undersensing will be made to the atrial Marker Channel data received from the IMD. The original Marker Channel may be displayed by programmer 30 according to the data received from the IMD (or corrected for any detected oversensing).

If any of the undersensing detection criteria are met, however, a median atrial sensed event interval is computed from all event intervals known to be true AS intervals included in the atrial channel recording at block 412. At block 416, the programmer identifies each AS event leading (at the beginning of) a long interval detected as an atrial undersensing interval (i.e. meeting undersensing detection criteria). In an adjusted Marker Channel display, an event identification marker is inserted at the end of the computed median atrial sensed event interval after the leading event at block 418. This inserted event marker marks the location of an undersensed event. Alternatively, if a P-wave morphology is identified on the EGM signal, an event marker may be inserted at a time point corresponding to a fiducial point of the P-wave morphology. In yet another embodiment, an event marker may be inserted midway between a leading event and a trailing event bounding the interval detected as an undersensing interval or at a median event interval earlier than a trailing sensed event.

In another approach, a median P-R interval may be determined from measured P-R intervals known to correspond to sensed events likely to be "true" P-waves and R-waves. If there is a long PP interval corresponding to an undersensed interval, during which an R-wave occurs unaccompanied by a corresponding P-wave, then an atrial event marker is inserted following the leading P-wave at the median P-R interval.

In some cases, more than one undersensed event could occur during an undersensing interval. In this situation, more than one event marker may be inserted in the undersensing interval, e.g. spaced apart from a previously inserted marker at the median atrial sensed event interval.

At block 420, a time stamp of the inserted event marker(s) is added to the time stamps of other sensed events in the recorded episode. After adding an event marker for each of the undersensed intervals detected, the events are renumbered consecutively from the beginning to the end of the episode at block 422.

Event intervals are recomputed after inserting the event marker(s) at block 424. These event intervals include an interval immediately preceding and immediately following an inserted marker. In some embodiments, event intervals recomputed after inserting event markers include cross-chamber event intervals, e.g. an R-P interval and/or a P-R interval. As such, cross-chamber event intervals may be computed at block 426 using the new event time stamp applied to an inserted marker at block 420. At block 428, an adjusted Marker Channel display is generated displaying annotated logic level event identification markers including the inserted event markers, recomputed event intervals, and renumbering of consecutive event markers.

Figure 6:
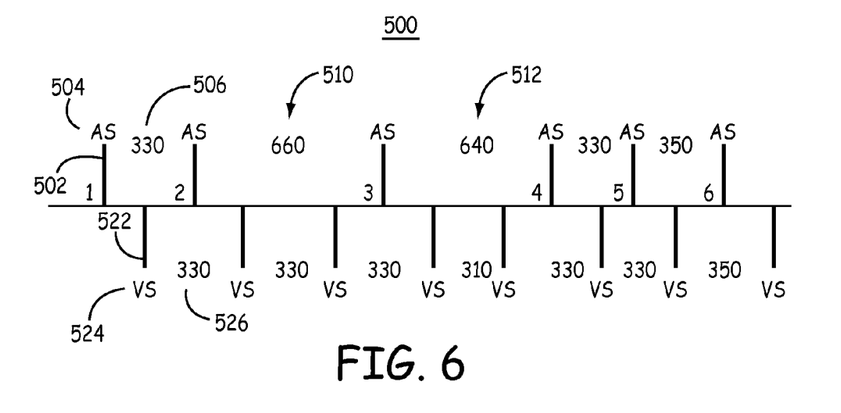
FIG. 6 is a depiction of a display of a Marker Channel showing encoded event identification markers as originally transmitted from an IMD to a programmer according to one embodiment.

FIG. 6 is a depiction of a display 500 of a Marker Channel showing encoded event identification markers as originally transmitted from an IMD 10 to a programmer 30 according to one embodiment. Display 500 includes atrial sense logic markers 502 labeled with "AS" annotations 504 and ventricular sense logic markers 522 labeled with "VS" annotations 524. Measurements of atrial event intervals 506 and ventricular event intervals 526 are labeled in milliseconds. The AS event markers 502 are numbered consecutively, 1 through 6, from the beginning to the end of the record.

Atrial event intervals 510 and 512 are approximately twice as long as other atrial event intervals 506, and the event pattern of PRR corresponding to one AS event with two subsequent VS events and no intervening AS event provide evidence that would be detected as undersensing of atrial events by reclassification module 140 of programmer 30.

Figure 7:
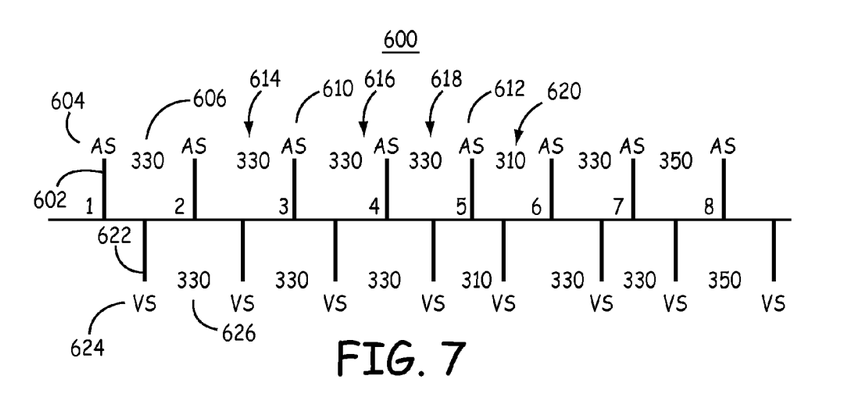
FIG. 7 is a depiction of a display of an adjusted Marker Channel showing encoded event identification markers and associated event interval measurements that have been corrected in response to detecting atrial undersensed events.

FIG. 7 is a depiction of an adjusted Marker Channel display 600 showing encoded event identification markers and associated event interval measurements that have been adjusted in response to detecting atrial undersensing. The AS event markers 602, AS annotations 604, AS event interval measurements 606, VS event markers 622, VS annotations 624, and VS event interval measurements 626 correspond to those shown in the original Marker Channel display 500 shown in FIG. 6 with the exceptions of inserted annotated AS event markers 610 and 612 and re-computed AS event intervals 614, 616, 618, and 620. After detecting and confirming suspected atrial undersensing at intervals 510 and 512 in the original Marker Channel display 500, the programmer 30 inserts annotated AS markers 610 and 620. For the episode shown, the median AS interval is 330 ms. The inserted event markers 610 and 612 are inserted at 330 ms after the leading AS event of the respective undersensing intervals 510 and 512.

Now instead of two long AS event intervals 510 and 512 as shown in display 500 of FIG. 6, four shorter intervals 614 through 620 are recomputed and resulting AS interval measurements are displayed in ms in FIG. 7. The AS event markers are renumbered consecutively, 1 through 8, from beginning to end of the adjusted Marker Channel display 600.

In this embodiment, the adjusted Marker Channel display 600 displays the inserted AS event markers 610 and 612 and event interval measurements 614 through 620 without any distinct formatting to differentiate the adjusted markers and event intervals from the original markers and event intervals. A user interacting with programmer 30 may select either the original Marker Channel display 500 or the adjusted Marker Channel display 600, toggle between the original and adjusted displays 500 and 600 or select simultaneous display of the original and adjusted displays 500 and 600 in various embodiments. While not shown in FIGS. 6 and 7, it is recognized that the Marker Channel displaying encoded event identification markers may be shown simultaneously with a corresponding EGM recording.

Figure 8:
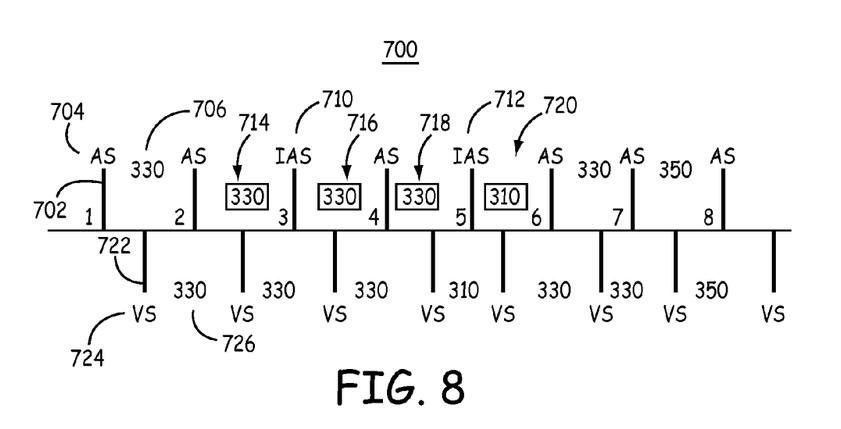
FIG. 8 is a depiction of a display of an adjusted Marker Channel showing encoded event identification markers and associated event interval measurements that have been corrected in response to detecting atrial undersensed events using distinctive formatting.

FIG. 8 is a depiction of an adjusted Marker Channel display 700 showing encoded event identification markers and associated event interval measurements that have been adjusted in response to detecting atrial undersensing according to an alternative embodiment. The inserted event markers and recomputed event intervals are formatted to distinguish them from original Marker Channel data. The AS event markers 702, AS annotations 704, AS event interval measurements 706, VS event markers 722, VS annotations 724, and VS event interval measurements 726 correspond to those shown in the original Marker Channel display 500 shown in FIG. 6 with the exceptions of inserted annotated AS event markers 710 and 712 and re-computed AS event intervals 714, 716, 718, and 720. After detecting and confirming suspected atrial undersensing at intervals 510 and 512 shown in the original Marker Channel display 500, the adjusted event identification encoder 142 inserts annotated AS markers 710 and 712.

In FIG. 7, the inserted event markers 610 and 612, corresponding AS annotations, and newly computed interval measurements 614-620 are shown in the adjusted Marker Channel display 600 without formatting that distinguishes the inserted markers and re-computed event intervals from the original markers and intervals. In FIG. 8, the adjustments to the original Marker Channel display are formatted in a manner to distinguish the inserted markers 710 and 712 from the original AS event markers 702. In the example shown, the inserted AS event markers 710 and 712 are displayed with a hashed-line logic level marker and a distinct annotation IAS (inserted atrial sense) to distinguish the inserted markers from original markers 702 on the atrial channel. In other examples, the inserted atrial sense event markers 710 and 712 may be formatted using a different color, different level or height, different shape, or different line weight of the logic level event marker.

Additionally or alternatively, the inserted event marker annotations may be provided as a different abbreviation than the "AS" annotation applied to the original atrial sensed events. Different abbreviations for the annotations could be used, such as the "IAS" annotation shown or "AUS" (atrial undersensed event). In other examples, the "AS" annotation may be used but highlighted using a different color, font size, font style, bold text or other text feature to distinguish the inserted annotated event marker from the original AS event marker annotations 704.

In addition to or alternatively to distinctively formatting the annotations and/or logic level markers of the inserted event markers 710 and 712, the recomputed event interval measurements 714 through 720 may be formatted in a manner to distinguish the recomputed intervals from original event intervals 706. The interval measurements 714 through 720 may be displayed in a different font, style, size, color, shading, highlighting or other distinguishing text feature.

A user interacting with programmer 30 may select a preferred formatting for distinguishing adjusted event markers, in this case inserted event markers corresponding to undersensed events, from original sensed event markers. The user may select between a display of the original Marker Channel as shown in FIG. 6, an adjusted Marker Channel display 600 as shown in FIG. 7 without distinctive formatting of adjusted event markers and event interval measurements, and an adjusted Marker Channel display 700 as shown in FIG. 8 including distinctive formatting to distinguish adjusted event markers and event interval measurements from original event markers and intervals.

Figure 9:
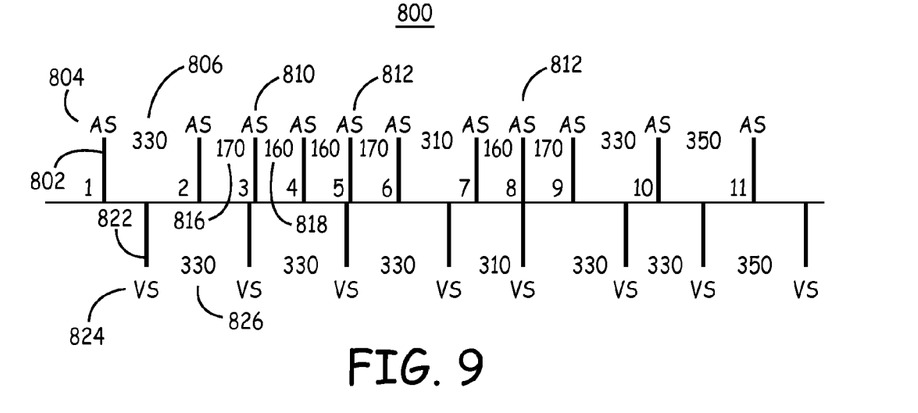
FIG. 9 is another example depiction of a display of a Marker Channel showing encoded event identification markers as originally transmitted from an IMD to a programmer.

FIG. 9 is another example depiction of a display 800 of a Marker Channel showing encoded event identification markers as originally transmitted from an IMD 10 to a programmer 30. Display 800 includes atrial sense logic markers 802 labeled with AS annotations 804, AS event interval measurements 806, ventricular sense logic markers 822 labeled with VS annotations 824, and VS event interval measurements 826. The AS event markers 802 are shown numbered consecutively, from 1 through 11, from the beginning to the end of the record.

AS event markers 810, 812, and 814 occur substantially simultaneously with VS event markers and are associated with short event intervals, e.g. intervals 816 and 818, immediately preceding and immediately following these AS event markers 810, 812 and 814. The event patterns, event intervals, and EGM morphology may be analyzed to detect whether these AS events at markers 810, 812, and 814 are oversensed FFRWs.

Figure 10:
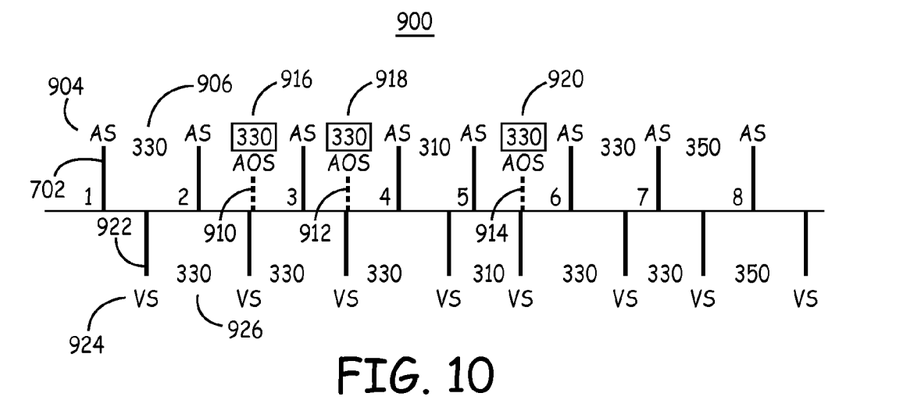
FIG. 10 is a depiction of a display of an adjusted Marker Channel showing encoded event identification markers and associated event interval measurements that have been corrected in response to detecting atrial oversensed events.

FIG. 10 is a depiction of a display 900 of an adjusted Marker Channel showing encoded event identification markers and associated event interval measurements that have been adjusted in response to detecting atrial oversensed events. In this example, the adjusted event markers associated with oversensed events are formatted to distinguish them from "true" event markers. The AS event markers 902, AS annotations 904, AS event interval measurements 906, VS event markers 922, VS annotations 924, and VS event interval measurements 926 correspond to those shown in the original Marker Channel display 800 shown in FIG. 9 with the exceptions of reformatting the AS event markers 910, 912 and 914 to distinguish these events as oversensed events.

Distinctive formatting of the adjusted markers 910, 912 and 914 may include altered line type of the marker (hashed, dotted, etc. as compared to solid line) or a marker phantom in the form of an outline or shadow of the original marker, or different line color, line weight, and/or logic level. Additionally or alternatively, the annotation of the event markers confirmed as being oversensed events may be adjusted by changing the abbreviation from "AS" to "AOS" (atrial oversense event), "FFRW", or another annotation to distinguish the oversensed event from a true atrial sensed event. Other adjustments to the annotation may include a distinct font, color, font size, font style, or highlighting of the annotation text.

The event interval measurements 916, 918 and 920 are recomputed ignoring the events 910, 912, and 914, using the leading and trailing "true" AS events. The recomputed event interval measurements 916, 918 and 920 may be displayed using the same formatting as an original event interval measurement 906 or using a distinct formatting, such as distinct font, font size, font style, color, highlighting or other feature to distinguish the recomputed event intervals 916, 918, and 920 from original event intervals. The event markers 902 of "true" AS events are consecutively renumbered, from 1 through 8, from the beginning of the record to the end, skipping the reformatted oversensed event markers 910, 912, and 914.

In another example, the event markers 910, 912 and 914 confirmed to be oversensed events may be removed entirely from the adjusted Marker Channel display 900. Recomputed event intervals 916, 918 ad 920 may be displayed. The adjusted Marker Channel display may have an appearance similar to the original Marker channel display 800 with the oversensed event markers 810, 812, and 814 entirely removed, associated event interval measurements recomputed, and "true" event markers consecutively renumbered.

A user interacting with programmer 30 may select a preferred formatting for distinguishing adjusted event markers associated with oversensed events. The user may select between a display of the original Marker Channel 800 as shown in FIG. 9, an adjusted Marker Channel display 900 as shown in FIG. 10 with distinctive formatting of event markers and/or event interval measurements associated with confirmed oversensed events, and an adjusted Marker Channel display with oversensed event markers removed and recomputed event interval measurements displayed with or without distinctive formatting for distinguishing recomputed event interval measurements from original event interval measurements shown in the display. As such, a user may select between an adjusted Marker Channel display with special formatting of adjusted event markers and/or intervals or no special formatting of adjusted event markers and/or intervals.

Thus, a system and method have been presented in the foregoing description with reference to specific embodiments for generating and displaying a corrected display of encoded event identification markers and associated event intervals. It is appreciated that various modifications to the referenced embodiments may be made without departing from the scope of the disclosure as set forth in the following claims.

The invention claimed is:

1. A system for generating a display of post-processed sensing data associated with identification of a cardiac event, comprising:
   an implantable medical device for sensing cardiac signals and generating and storing sensing data, wherein the sensing data includes sensed cardiac events;
   a processor configured to receive the sensing data, determine if one of an undersensing criterion and an oversensing criterion is met in response to the received sensing data, and detect an event as being one of an undersensed event and an oversensed event in response to a criterion being met;
   an encoder configured to generate an episode display comprising event identifying codes in response to the sensing data received from the implantable medical device and to produce an adjusted episode display in response to an event being identified as being one of an undersensed event and an oversensed event; and
   a display to display the adjusted episode display, wherein the encoder is further configured to compute an interval between sensed events from the sensing data and to recompute a time interval associated with an event that is identified as one of an undersensed and an oversensed event, and producing an adjusted episode display comprises displaying the recomputed interval, and wherein displaying the recomputed interval comprises formatting the displayed recomputed interval to indicate that the interval is a recomputed interval distinguishable from an originally computed interval between sensed events from the sensing data.

2. The system of claim 1, wherein producing an adjusted episode display comprises removing an event identifying code in response to detecting an event as being an oversensed event.

3. The system of claim 1, wherein producing the adjusted episode display comprises inserting an event identifying code comprising an annotated event marker signal in response to detecting an event as being an undersensed event.

4. The system of claim 1, wherein producing an adjusted episode display comprises modifying an event identifying code identifying an event detected as being one of an undersensed event and an oversensed event.

5. The system of claim 4, wherein modifying comprises one of modifying an event identification marker and modifying an event identification annotation identifying the event detected as one of an undersensed and an oversensed event.

6. The system of claim 1, wherein detecting an undersensed event comprises detecting an undersensed P-wave and detecting an oversensed event comprises detecting a far-field R-wave, and wherein the encoder is configured to insert an event identifying code at an estimated location of a detected undersensed P-wave and remove an event identifying code corresponding to a detected far-field R-wave.

7. The system of claim 1, further comprising a user interface to enable a user to interact with the system, wherein the encoder and the display are configured to display an adjusted episode display format selection selectable by the user via the user interface, the selection comprising a formatted adjusted episode display distinguishing an adjusted event identification code from an original event identifying code.

8. The system of claim 1, further comprising a user interface to enable a user to interact with the system,
wherein the encoder, the user interface and the display are configured to cooperatively enable a user to toggle between an original episode display and the adjusted episode display.

9. A method for generating a display of post-processed sensing data associated with identification of a cardiac event, comprising:
sensing cardiac signals and generating and storing sensing data wherein the sensing data includes sensed cardiac events;
determining whether one of an undersensing criterion and an oversensing criterion is met in response to the sensing data, detect an event as being one of an undersensed event and an oversensed event in response to a criterion being met;
generating an episode display comprising event identifying codes in response to the sensing data and producing an adjusted episode display in response to an event being identified as being one of an undersensed event and an oversensed event;
computing an interval between sensed events from the sensing data and recomputing an interval associated with an event that is detected as one of an undersensed and an oversensed event; and
displaying the recomputed interval in the adjusted episode display, wherein displaying the recomputed interval further comprises formatting the recomputed interval to indicate that the interval is a recomputed interval distinguishable from an originally computed interval between sensed events from the sensing data.

10. The method of claim 9, wherein producing an adjusted episode display comprises removing an event identifying code in response to detecting an event as being an oversensed event.

11. The method of claim 9, wherein producing the adjusted episode display comprises inserting an event identifying code comprising an annotated event marker signal in response to detecting an event as being an undersensed event.

12. The method of claim 9, wherein producing an adjusted episode display comprises modifying an event identifying code identifying an event detected as being one of an undersensed event and an oversensed event.

13. The method of claim 12, wherein modifying an event identifying code comprises one of modifying an event identification marker and modifying an event marker annotation identifying the event detected as one of an undersensed and an oversensed event.

14. The method of claim 9, wherein detecting an undersensed event comprises detecting an undersensed P-wave and detecting an oversensed event comprises detecting a far-field R-wave, and wherein producing an adjusted episode display comprises:
inserting an event identifying code at an estimated time location of a detected undersensed P-wave; and
removing an event identifying code corresponding to a detected far-field R-wave.

15. The method of claim 9, further comprising displaying a formatted adjusted episode in response to a user input, the formatted adjusted episode display comprising formatting for distinguishing an adjusted event identification code from an original event identifying code.

16. The method of claim 9, further comprising toggling between a display of an original episode display and the adjusted episode display in response to a user input.

17. A non-transitory computer-readable medium comprising instructions for causing a processor of a medical device system to perform a method, the method comprising:
sensing cardiac signals and generating and storing sensing data wherein the sensing data includes sensed cardiac events;
determining whether one of an undersensing criterion and an oversensing criterion is met in response to the received sensing data, detect an event as being one of an undersensed event and an oversensed event in response to a criterion being met;
generating an episode display comprising event identifying codes in response to the sensing data and producing an adjusted episode display in response to an event being identified as one of an undersensed event and an oversensed event;
computing an interval between sensed events from the sensing data and recomputing an interval associated with an event that is detected as one of an undersensed and an oversensed event; and
displaying the recomputed interval in the adjusted episode display, wherein displaying the recomputed interval further comprises formatting the recomputed interval to indicate that the interval is a recomputed interval distinguishable from an originally computed interval between sensed events from the sensing data.

* * * * *